United States Patent [19]
Graetz et al.

[11] Patent Number: 5,617,846
[45] Date of Patent: Apr. 8, 1997

[54] METHOD OF CONTROLLING A RESPIRATOR FOR TREATMENT OF SLEEP APNEA AND DEVICE FOR CARRYING OUT THE METHOD

[75] Inventors: Bernd Graetz, Schenefeld; Jörg Maurer, Oststeinbek, both of Germany

[73] Assignee: Gottlieb Weinmann Geräte für Medizin und Arbeitsschutz GmbH & Co., Hamburg, Germany

[21] Appl. No.: 525,963

[22] Filed: Sep. 8, 1995

[30] Foreign Application Priority Data

Sep. 8, 1994 [DE] Germany .......................... 94 14 568.7

[51] Int. Cl.$^6$ ................................................ A61M 16/00
[52] U.S. Cl. ............................ 128/204.21; 128/204.23; 128/204.26; 128/848
[58] Field of Search .......................... 128/204.18, 204.21, 128/204.23, 204.26, 848, 205.25, 207.18

[56] References Cited

U.S. PATENT DOCUMENTS

| | | | |
|---|---|---|---|
| 5,148,802 | 9/1992 | Sanders et al. | 128/204.18 |
| 5,239,995 | 8/1993 | Estes et al. | 128/204.23 |
| 5,313,937 | 5/1994 | Zdrojkowski | 128/202.22 |
| 5,335,654 | 8/1994 | Rapoport | 128/204.23 |
| 5,353,788 | 10/1994 | Miles | 128/204.23 |
| 5,390,666 | 2/1995 | Kimm et al. | 128/204.26 |
| 5,398,682 | 3/1995 | Lynn | 128/633 |
| 5,433,193 | 6/1995 | Sanders et al. | 128/204.18 |
| 5,438,980 | 8/1995 | Phillips | 128/204.23 |
| 5,443,075 | 8/1995 | Holscher | 128/725 |

OTHER PUBLICATIONS

"Erfahrungen mit der Oszilloresistometrie in Ergänzung der Spirometrie in der praoperativen Funktionsdiagnostik alter Menschen," Zeitschrift fuer Erkankungen der Atmungsorgane 1984, 163(2) pp. 146–152, ISSN 0303–657X.

Primary Examiner—V. Millin
Assistant Examiner—Eric P. Raciti
Attorney, Agent, or Firm—Robert W. Becker & Associates

[57] ABSTRACT

For controlling a respirator for treatment of sleep apnea, a patient's oscillatory pressure amplitude, which corresponds to a patient's breathing resistance is continuously measured, and the individual breathing resistance value (base value) of a patient's pressure amplitude is determined, by oscilloresistometry (oscillatory resistance measuring=ORM). If deviations from this base value occur, the patient is supplied with respiratory gas under pressure and the gas supply is terminated or minimized as soon as the base value is again reached or almost reached.

10 Claims, 1 Drawing Sheet

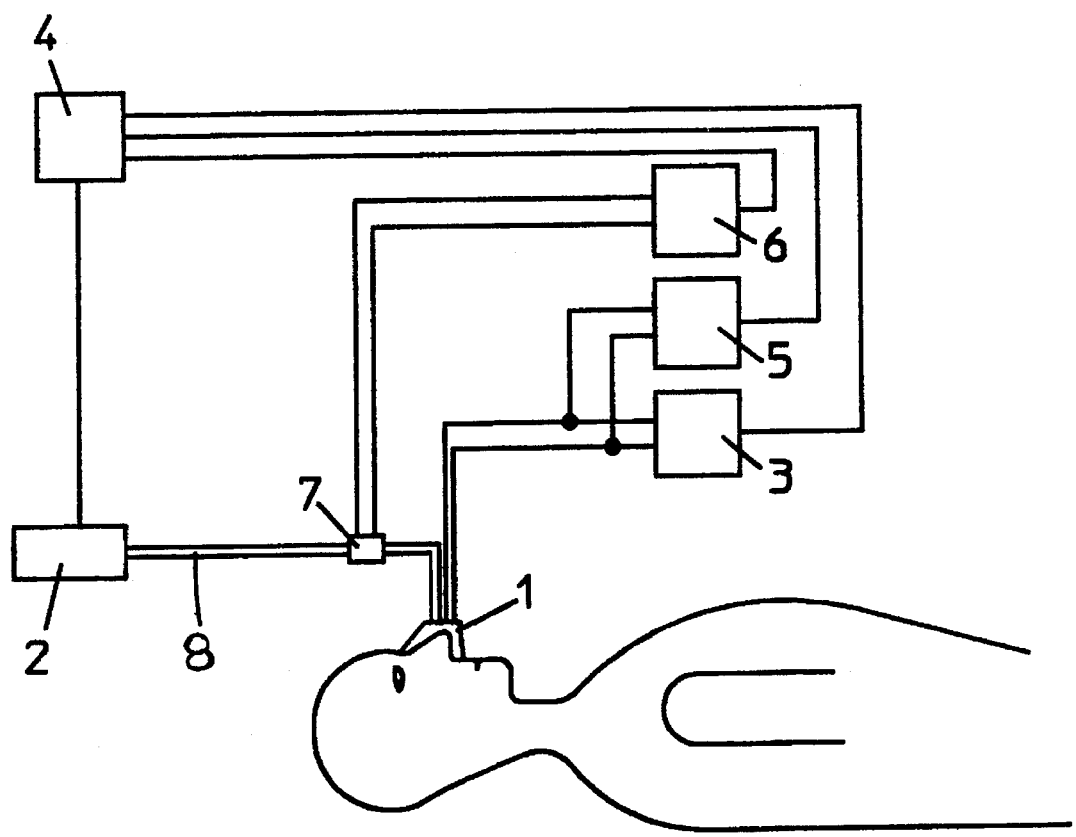

METHOD OF CONTROLLING A RESPIRATOR FOR TREATMENT OF SLEEP APNEA AND DEVICE FOR CARRYING OUT THE METHOD

BACKGROUND OF THE INVENTION

The present invention relates to a method of controlling a respirator for treatment of sleep apnea and a device for carrying out the method.

A not insignificant number of people suffer from sleep disorders which have an impact on those people's well-being during the day and which partly have a significant effect on their social and professional efficiency as well as on their quality of life. One of these sleep disorders is sleep apnea, which is primarily treated with the so-called CPAP-therapy (CPAP=Continuous Positive Airway Pressure) by continuously supplying an air stream of a respiration gas to the patient during his sleep via a nasal mask. Via a tube, the mask is connected with a device for respiration comprising a ventilator that generates a gas stream with an overpressure of 5 to 20 mbar.

The gas stream is supplied to the patient either at a constant pressure or it is lowered to a lower pressure level in order to ease the breathing effort of the patient during exhaling. Although sleep apneas occur only briefly and are only a very small portion of the sleeping period, the ventilator in both methods runs during the entire sleeping period (night) and thus renders the acceptance of this sleep apnea treatment difficult.

It is therefore an object of the present invention to improve the CPAP therapy to become patient friendly.

BRIEF DESCRIPTION OF THE DRAWING

This object, and other objects and advantages of the present invention, will appear more clearly from the following drawing, which illustrates one exemplary embodiment of the invention.

SUMMARY OF THE INVENTION

The inventive method for controlling a respirator is characterized primarily by continuously measuring the oscillatory pressure amplitude, which corresponds to the patient's breathing resistance, by means of oscilloresistometry (oscillatory resistance measuring=ORM). After determining the individual breathing resistance (base value) of the pressure amplitude, then when deviations from this value occur the patient is supplied with respiratory gas under pressure; the gas supply is terminated or minimized as soon as the base value is again reached or almost reached.

With the inventive method for controlling and regulating a respirator for the treatment of sleep apnea patients, this device is only activated, i.e. respiratory gas is supplied to the patient only, if the breathing activity of the patient is affected by an apnea or if the breathing resistance—and thus also the measured oscillatory pressure amplitude—is altered by a developing apnea. A disruption of the respiratory activity of the patient is accompanied by an alteration of the patient's breathing resistance. This resistance is reliably and reproducibly determined in a simple way by means of altering the oscillatory pressure amplitude without affecting the patient's well-being. The oscillatory pressure amplitude is the control parameter for turning the therapy device on and off so that an under-supply of oxygen to the patient does not occur.

The well-being of the patient can be further improved by an advantageous further development of the inventive method with which respiratory gas is continuously supplied to the patient at a moderate base pressure of 3 to 5 mbar and the gas pressure is increased when deviations from the individual breathing resistance value (base value) occur and it is lowered to the base pressure as soon as the base value is approximately reached. This continuous supply of gas not only supports the breathing of the patient conveniently but also has a positive effect on the determination of the parameter required for controlling the pressure of the respiratory gas.

In a beginning apnea, contractions or expansions of a patient's airways lead to alterations in the phase angle of the oscillatory pressure amplitude and of the breathing flow compared to the respective base values during a normal or undisturbed respiratory cycle. These undesired alterations can be countered by further expedient embodiments of the invention with which the phase angle of the pressure amplitude and/or the patient's breathing flow are used as additional control signals and/or regulating signals for the respirator in order to increase the pressure of the supplied respiratory gas in case of significant deviations of the respective individual base value that was determined at the beginning of the therapy until the base values are again reached or almost reached.

A respirator for carrying out the method according to the invention comprises a pressurized gas source that is expediently embodied as a ventilator and is connected with a breathing mask and is characterized by a device for continuously measuring the oscillatory pressure amplitude of a patient according to the ORM principle as well as by a control-regulating device that is adjustable to the individual base value of the oscillatory pressure amplitude, which corresponds to a patient's breathing resistance value, and that activates the pressure gas source such that respiratory gas is supplied to the patient if significant deviations from the base value of the breathing resistance occur.

As a further control element for activating the pressurized gas source, the respirator can be provided in an expedient embodiment with a device for measuring and determining the phase angle of the pressure amplitude and/or with a device embodied as a pneumotachograph or a metering orifice for determining the breathing flow of the patient.

In a further embodiment of the invention the respirator can additionally be provided with a pressure controller for the respiratory gas, adjustable to the patient's needs, by means of which the acceptance of the therapy device is increased since the patient is being provided with artificial respiration at a constant pressure that is convenient for him if the oscillatory pressure amplitude and/or the phase angle of the pressure amplitude and/or the patient's breathing flow correspond with the base value(s).

DESCRIPTION OF PREFERRED EMBODIMENTS

Referring now to the drawings in detail, the respirator for treatment of sleep apnea is provided with a breathing mask 1 that can be placed over a patient's nose and that is connected with a pressurized or compressed gas source 2 embodied as a fan or ventilator via a breathing tube 8. In the interior of the breathing mask 1, the sensors (not illustrated) of a device 3 for continuously measuring the oscillatory pressure amplitude according to the ORM principle are provided. The pressurized gas source 2 is activated in such a way by a control-regulating device 4, which is connected with the device 3 and is adjustable to the individual base value of the oscillatory pressure amplitude that corresponds to the patient's breathing resistance, that respiratory gas is supplied to the patient upon the occurrence of significant deviations from the base value of the pressure amplitude. A metering orifice 7 is inserted into a part of the breathing tube 8. The metering orifice 7 detects the breathing flow and transmits the respective data to the control-regulating device 4 via a measuring device 6 for a further influence on the pressurized gas source 2. The interior of the breathing mask 1 is additionally provided with the sensors (not illustrated) of another device 5 for measuring the phase angle of the pressure amplitude. The device 5 transmits signals to the control-regulating device 4 that serve as additional regulating parameter upon activation of the pressure source 2.

The present invention is, of course, in no way restricted to the specific disclosure of the specification and drawing, but also encompasses any modifications within the scope of the appended claims.

What we claim is:

1. A method of controlling a respirator for the treatment of sleep apnea, comprising the steps of:
   determining the individual breathing resistance of a patient to obtain a base value of the oscillatory pressure amplitude, which corresponds to said breathing resistance of said patient;
   continuously measuring, by oscilloresistometry or oscillatory resistance measuring, the oscillatory pressure amplitude of said patient;
   supplying respiratory gas under pressure to said patient if deviations from said base value occur; and
   terminating or minimizing said supply of respiratory gas as soon as said base value is again reached or nearly reached.

2. A method according to claim 1, which includes the steps of measuring the breathing flow of said patient, and upon the occurrence of significant deviations from an individual base value thereof as determined at the beginning of a therapy, increasing the pressure of said respiratory gas until such base value is again reached or nearly reached.

3. A method according to claim 1, which includes the steps of continuously measuring the phase angle of said pressure amplitude of said patient, and upon the occurrence of significant deviations from an individual base value thereof as determined at the beginning of a therapy, increasing the pressure of said respiratory gas until such base value is again reached or nearly reached.

4. A method according to claim 3, wherein said step of continuously measuring the phase angle of said pressure amplitude of said patient comprises determining said phase angle from signals from a device for measuring said oscillatory pressure amplitude and from signals from a metering orifice or pneumotachograph that is disposed in a gas feed line that connects a source of said respiratory gas to a breathing mask for said patient.

5. A method according to claim 1, which includes the steps of continuously supplying respiratory gas to said patient at a base pressure of about 3 to 5 mbar, raising said gas pressure when deviations from said base value occur, and lowering said gas pressure back to said base pressure as soon as said base value is again reached or nearly reached.

6. An apparatus for carrying out said method claim 5, comprising:
   a breathing mask for a patient;
   a pressurized gas source connected to said mask;
   a device for continuously measuring, by the oscillatory resistance measuring principle, he oscillatory pressure amplitude, which corresponds to the breathing resistance, of said patient; and
   a control-regulating device that is adjustable to a base value of said oscillatory pressure amplitude and activates or controls said pressurized gas source for supplying respiratory gas to said patient at an increased pressure when significant deviations from said base value occur.

7. An apparatus according to claim 6, which includes a pressure regulator for said respiratory gas that is adjustable in conformity with said patient's needs.

8. An apparatus according to claim 6, wherein said pressurized gas source is a ventilator.

9. An apparatus according to claim 6, which includes a device for continuously measuring and determining the phase angle of said pressure amplitude, such device being connected to said control-regulating device, which comprises means that can be set to an individual base value of said phase angle of said patient.

10. An apparatus according to claim 9, which includes: a gas feed line that connects said pressurized gas source to said mask; a metering orifice or pneumotachograph disposed in said gas feed line; and a measuring device connected to said metering orifice or pneumotachograph for continuously measuring and determining the breathing flow of said patient, such measuring device being connected to said control-regulating device, which comprises means that can be set to an individual base value of said breathing flow of said patient.

* * * * *